United States Patent [19]

Schickaneder et al.

[11] Patent Number: 4,738,960
[45] Date of Patent: Apr. 19, 1988

[54] 1,3,4-THIADIAZOLE DERIVATIVES AND PHARMACEUTICAL PREPARATIONS USEFUL AS INHIBITORS FOR HISTAMINE-$H_2$ RECEPTORS

[75] Inventors: Helmut Schickaneder, Eckental; Rolf Herter, Schwabach; Kurt Wegner, Mainz; Walter Schunack, Berlin; Istvan Szelenyi, Schwaig; Stefan Postius; Kurt H. Ahrens, both of Nuremberg, all of Fed. Rep. of Germany

[73] Assignee: Ludwig Heumann & Co. GmbH, Nuremberg, Fed. Rep. of Germany

[21] Appl. No.: 799,691

[22] Filed: Nov. 19, 1985

[30] Foreign Application Priority Data

Apr. 12, 1985 [DE] Fed. Rep. of Germany ....... 3513184

[51] Int. Cl.$^4$ ..................... A61K 31/38; A61K 31/41; C07D 285/12
[52] U.S. Cl. .................... 514/212; 514/269; 514/317; 514/318; 514/326; 514/340; 514/363; 514/422; 540/597; 540/601; 540/603; 544/316; 546/192; 546/193; 546/194; 546/209; 546/277; 548/141; 548/518
[58] Field of Search ........ 540/597, 601, 603; 544/316; 546/191–194, 209, 277; 548/141, 518; 514/212, 269, 317, 318, 326, 340, 363, 422

[56] References Cited

U.S. PATENT DOCUMENTS

| 4,440,933 | 4/1984 | Montzka | 546/193 |
| 4,447,440 | 5/1984 | Busse | 514/381 |
| 4,578,471 | 3/1986 | Crenshaw et al. | 540/480 |
| 4,587,254 | 5/1986 | Toyofuku et al. | 546/209 |
| 4,600,779 | 7/1986 | Crenshaw et al. | 540/480 |

FOREIGN PATENT DOCUMENTS

| 0065658 | 4/1982 | European Pat. Off. | 548/337 |
| 3341750 | 5/1985 | Fed. Rep. of Germany | 548/267 |

OTHER PUBLICATIONS

Morrison and Boyd, *Organic Chemistry*, 5/74, pp. 738–740.
Noller, *Chemistry of Organic Chemistry*, 1965, p. 512.
Chemical Abstracts, 102:113506n (JP196,879/1984).

*Primary Examiner*—Henry R. Jiles
*Assistant Examiner*—Zinna Northington

[57] ABSTRACT

1,3,4-Thiadiazole derivatives corresponding to the general formula I

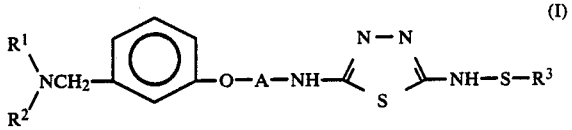

which constitute highly effective inhibitors for histamine-$H_2$ receptors are described. These compounds in addition have a cytoprotective action.

10 Claims, No Drawings

1,3,4-THIADIAZOLE DERIVATIVES AND PHARMACEUTICAL PREPARATIONS USEFUL AS INHIBITORS FOR HISTAMINE-H₂ RECEPTORS

This invention relates to new 1,3,4-thiadiazole derivatives which have a highly selective action on histamine-$H_2$ receptors, to processes for their preparation, to pharmaceutical preparations containing these compounds and to the use of these compounds in therapy.

Cimetidin and ranitidin have already been used in therapy as antiulcerative agents. Both these substances, however, have a relatively short half life and are therefore required to be administered in several daily doses of tablets with dose units of 160 to 300 mg each in a therapeutically fixed form. There continues, therefore, to be a need for antiulcerative agents which are more effective than cimetidin or ranitidin.

It is an object of the present invention to provide new substances which have a highly effective inhibitory action on histamine-$H_2$ receptors as well as a cytoprotective action. This problem is solved by the compounds according to the invention.

By virtue of their specific $H_2$-antagonistic activity, the compounds according to the invention inhibit gastric secretion when this has been stimulated by histamine agonistics [Ash and Schild, "Brit. J. Pharmacol. Chemother.", 27, 427 (1966) and Black et al., "Nature", 236, 385 (1971)]. The compounds according to the invention in addition have a cytoprotective action. The pharmacological activity of these compounds may be demonstrated on the perfused rat stomach by a modified method according to DE-OS No. 2 734 070 or by determining the $pA_2$-values in vitro on the atrium of the guinea-pig (see Ariens, "Molecular Pharmacology", Volume 1, Academic Press, New York 1964). The $H_2$-antagonistic action may also be demonstrated on waking Heidenhain-Pouch dogs by the method of Black et al., "Nature", 236, 385 (1971). The new compounds also antagonize the action of histamine on the frequency of contraction of the isolated right atrium of the guinea-pig but have no influence on histamine induced contractions of isolated, smooth gastrointestinal muscle when these contractions have been produced by $H_2$-agonists.

Since substances which inhibit histamine-$H_2$ receptors have an inhibitory action both on the basal gastric acid secretion and on the gastric acid secretion induced by gastrin, histamine, methacholine or food, they may be used for the treatment of peptic ulcers caused by excessive gastric acid secretion as well as for the treatment of hyperacidic gastritis.

The present invention relates to new 1,3,4-thiadiazole derivatives corresponding to the general formula I

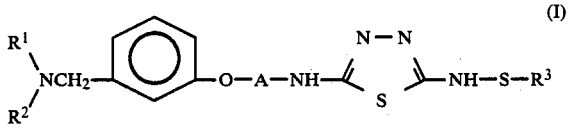

(I)

wherein $R^1$ and $R^2$, which may be identical or different, represent hydrogen, linear $C_1$-$C_{10}$-alkyl, polycycloalkyl, $C_1$-$C_3$-alkylamino or di-($C_1$-$C_3$-alkyl)amino or $R^1$ and $R^2$ together with the nitrogen atom to which they are attached may form a 5- to 10-membered alicyclic, heterocyclic ring containing nitrogen; A represents the group —$(CH_2)_n$— wherein n has the value 3 or 4, or —$CH_2$—$CH$=$CH$—$CH_2$—, and $R^3$ represents a straight chained or branched $C_1$-$C_6$-alkyl or $C_5$-$C_6$-cycloalkyl or unsubstituted or mono- or tri-substituted aryl or heteroaryl, and the physiologically acceptable salts thereof.

In the general formula I, the substituents represented by $R^1$ and $R^2$, which may be identical or different, may by a hydrogen atom, a straight chained $C_1$-$C_{10}$-alkyl group, preferably a straight chained $C_1$-$C_6$-alkyl group and most preferably a straight chained $C_1$-$C_3$-alkyl group, e.g. a methyl, ethyl or propyl group, a $C_5$ or $C_6$-cycloalkyl group, i.e. a cyclopentyl or cyclohexyl group, a $C_1$-$C_3$-alkylamino group, e.g. an n- or i-propylamino group, an ethylamino group or a methylamino group, the methylamino group being preferred, or a di-($C_1$-$C_3$-alkyl)amino group, preferably a diethyl or dimethylamino group. However, $R^1$ and $R^2$ together with the nitrogen atom to which they are attached may also form a 5- to 10-membered, nitrogen-containing alicyclic, heterocyclic ring optionally mono-substituted or disubstituted with a $C_1$-$C_3$-alkyl group. This ring may contain one or more further hetero atoms; for example, another nitrogen atom, an oxygen atom or a sulphur atom. The pyrrolidine, piperidine and homopiperidine ring are preferred examples of the 5- to 10-membered heterocyclic ring thus defined. Preferred examples of heterocyclic rings containing additional hetero atoms are the piperazine and morpholine ring. In the case of monosubstitution or disubstitution on the 5- to 10-membered, nitrogen-containing alicyclic, heterocyclic ring, each of the substituents is a $C_1$-$C_3$-alkyl group, preferably a methyl group. Thus, for example, the pyrrolidine, piperidine or homopiperidine ring may be substituted with a methyl group in the 2-, 3- or 4-position or, if it is disubstituted, the substitution with a methyl group may take place in the 2,5- or 2,6-positions. Examples of preferred nitrogen-containing 5- to 10-membered alicyclic, heterocyclic rings which are substituted include the 3-methylpyrrolidine, 3-methylpiperidine, 4-methylpiperidine and 3,5-dimethylpiperidine ring, the 3-methylpyrrolidine and 3-methylpiperidine ring being particularly preferred.

The symbol A denotes one of the following groups: —$(CH_2)_n$— or —$CH_2$—$CH$=$CH$—$CH_2$—, n denoting the integer 3 or 4, the value 3 being preferred.

$R^3$ denotes a straight chained or branched $C_1$-$C_6$-alkyl, preferably a $C_1$-$C_3$-alkyl, such as, for example, methyl, ethyl, propyl, isopropyl, butyl, isobutyl, n-pentyl, isopentyl, n-hexyl or isohexyl; or it may denote a $C_5$-$C_6$-cycloalkyl such as cyclopentyl or cyclohexyl.

The symbol $R^3$ may also denote an unsubstituted or mono- or tri-substituted aryl. Examples of aryl groups are the phenyl and naphthyl group, phenyl being preferred. The aryl group may be mono-, di or tri-substituted, in particular by a halogen such as chlorine or bromine, a straight chained or branched lower alkyl group, preferably a $C_1$-$C_4$-alkyl, in particular methyl, a lower alkoxy group or, trifluoromethyl nitrile. The terms "lower alkyl", "lower alkoxy", etc. are used here to denote groups having 1 to 6, preferably 1 to 4 carbon atoms in the alkyl moiety. In the case of monosubstitution, the substituent may be attached in the ortho-, meta- or para-position, the para-position being preferred. In the case of disubstitution, the ortho, para-positions (2,4-positions on the phenyl ring), and the ortho, ortho-positions (2,6-positions on the phenyl ring) are preferred.

Another meaning for $R^3$ is that of an unsubstituted or mono- or tri-substituted heteroaryl group. Examples of such heteroaryl groups include pyridyl, pyrimidinyl, thiazolyl and benzothiazolyl, the pyridyl and pyrimidinyl groups being preferred. The heteroaryl groups may be unsubstituted or they may be mono-, di- or tri-substituted with the same groups as those described above for aryl and in the same positions as described for aryl. Mono-substitution with a lower alkyl group, in particular a $C_1$-$C_4$-alkyl group is preferred.

The compounds according to the invention may be prepared by a process in which an amine corresponding to the general formula II

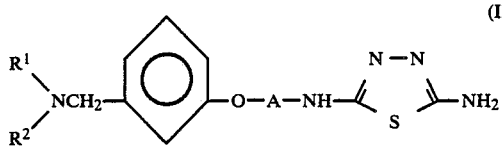
(II)

wherein $R^1$, $R^2$ and A have the meanings indicated above is reacted with, preferably, equimolar quantities of a sulphenyl halide corresponding to the general formula III

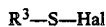 (III)

wherein Hal stands for a chlorine or bromine atom, preferably a chlorine atom, and $R^3$ has the meaning indicated above, in an inert solvent such as ether, tetrahydrofuran, dioxane or dimethylformamide, preferably tetrahydrofuran, by a basic catalyzed reaction at a temperature of from 0° C. to 20° C., preferably at 5° C. The bases used may be tertiary amines such as dimethylbenzylamine, triethylamine or pyridine. The reaction product is worked up in known manner, for example, by concentration of the reaction mixture by evaporation, crystallization and/or purification by column chromatography.

Preparation of the sulphenyl halide corresponding to the general formula III is carried out by methods known in the literature (see inter alia E. Kühle, "The Chemistry of Sulphenic Acids", Georg Thieme Verlag (1973)).

The amines corresponding to the general formula II are prepared in known manner. Thus, for example, a compound corresponding to the general formula VI

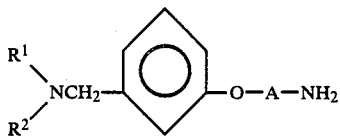
(VI)

wherein $R^1$, $R^2$ and A have the meanings indicated above may be reacted with a 1,3,4-thiadiazole corresponding to formula VII

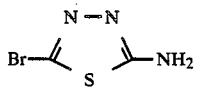
(VII)

(method of preparation analogous to that of G. Werber et al., "J. Heterocycl. Chem.", 14, 823 (1977)) in an inert solvent such as tetrahydrofuran or dioxane, using a basic catalyst. The base used is preferably triethylamine.

The compounds according to the invention may also be prepared by a process in which a compound corresponding to the general formula IV

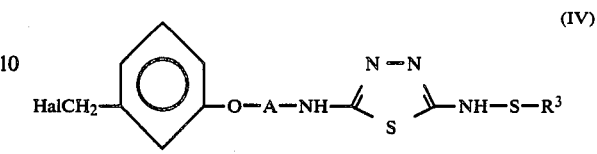
(IV)

wherein Hal stands for a chlorine or bromine atom and A and $R^3$ have the meanings indicated above, is reacted in an inert solvent, such as tetrahydrofuran or dioxane, with preferably equimolar quantities of an amine corresponding to the general formula V

(V)

wherein $R^1$ and $R^2$ have the meanings indicated above by a base-catalyzed reaction to produce a compound according to the invention corresponding to the general formula I.

The compound corresponding to the general formula IV is prepared by known methods. Thus, for example, an alcohol corresponding to formula VIII

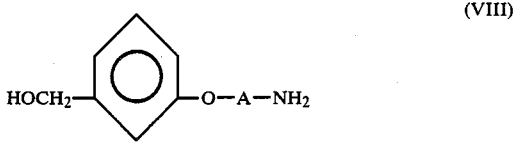
(VIII)

wherein A has the meaning indicated above may be reacted with a 1,3,4-thiadiazole corresponding to formula VII

(VII)

in an inert solvent such as tetrahydrofuran or dioxane by a base-catalyst reaction to produce a compound corresponding to the general formula IX

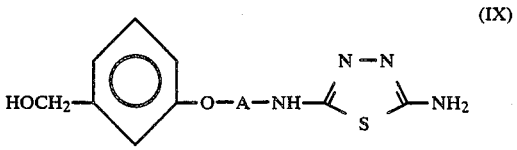
(IX)

wherein A has the meaning indicated above, the resulting compound being subsequently converted by means of a halogenating agent such as thionyl chloride into a compound corresponding to the general formula X

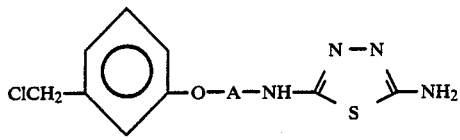

(X)

which compound of formula X is then reacted as described above with preferably equimolar quantities of a sulphenyl halide corresponding to the general formula III R³—S—Hal  (III)

wherein R³ has the meaning defined above, to produce a compound corresponding to the general formula IV.

The invention also covers the stereoisomeric compounds and physiologically acceptable salts of the above mentioned compounds. These salts may be prepared in known manner, for example with organic acids such as formic acid, acetic acid, propionic acid, phenylacetic acid, tartaric acid, citric acid, fumaric acid, methanesulphonic acid, embonic acid, etc.

The compounds according to the invention may be made up into any desired formulations for administration. The invention therefore also covers pharmaceutical preparations containing at least one compound according to the invention for use in human or veterinary medicine. Such pharmaceutical preparations may be prepared by the conventional methods, using one or more pharmaceutically acceptable carriers or diluents.

The compounds according to the invention may thus be formulated for oral, buccal, topical, parenteral or rectal administration, oral administration being preferred. For oral administration, the pharmaceutical agent may be made up into, for example, tablets, capsules, powders, solutions, syrups or suspensions which are prepared by the conventional methods using acceptable diluents. For buccal administration, the medicament may be provided in the form of tablets or sachets formulated in the usual manner.

The compounds according to the invention may also be formulated for parenteral administration by bolus injection or continuous infusion. Formulations for injection may be provided in the form of unit doses as ampoules or in multiple dose containers with added preservative.

The pharmaceutical preparations may assume the form of suspensions, solutions or emulsions in oily or aqueous carriers and may contain formulating auxiliaries such as suspension, stabilizing and/or dispersing agents. Alternatively, the active ingredient may be provided in powder form to be reconstituted before use with a suitable carrier such as, for example, sterile, pyrogen-free water.

The compounds according to the invention may also be formulated for rectal administration, for example in the form of suppositories or retention enemas which may contain, for example, conventional suppository excipients such as cocoa butter or other glycerides.

For topical application, the compounds according to the invention may be formulated as ointments, creams, gels, lotions, powders or sprays in the usual manner.

For oral administration, a suitable daily dose of compounds according to the invention is 1 to 4 doses amounting to a total of 5 mg to 1 g per day, preferably 5 to 250 mg per day, depending on the condition of the patient. In some cases, it may be necessary to deviate from these quantities, depending on the individual response to the active ingredient or on the nature of its formulation and the time or interval of time of administration. Thus, in some cases, for example, it may be sufficient to administer less than the minimum quantity indicated above whereas in others it may be necessary to exceed the upper limit.

The invention will now be described in more detail with the aid of Examples.

EXAMPLE 1

Method A

2-[3-[3-(Piperidinomethyl)phenoxy]propylamino]-5-pyridine-2-sulphenamido-1,3,4-thiadiazole (a) Preparation of N-[3-[3-(1-piperidinomethyl)-phenoxy]propyl]-1,3,4-thiadiazole-2,5-diamine 0.57 g (2.3 mmol) of 1-Amino-[3-[3-(1-piperidinomethyl)phenoxy]-propane, 0.35 ml of triethylamine and 0.42 g (2,3 mmol) of 5-bromo-1,3,4-thiadiazole-2-amine are heated under reflux in 20 ml of THF for 3 hours. Solid triethylammonium bromide is filtered off, the filtrate is concentrated by evaporation and the residue is purified by preparative layer chromatography.

Yield: 0.25 g (30% of theoretical); melting point: 158°–159° C.

$C_{17}H_{25}N_5OS$ (347.5) Calculated: C, 58.8; H, 7.25; N, 20.2. Found: C, 58.8; H, 7.28; N, 20.0.

(b) Preparation of 2-[3-[3-(piperidinomethyl)phenoxy]propylamino]-5-pyridine-2-sulphenamido-1,3,4-thiadiazole

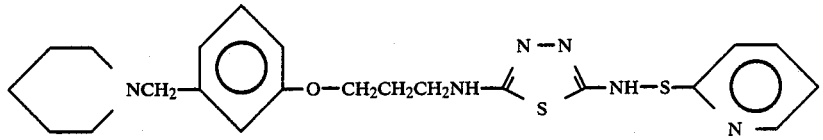

3.47 g (10 mmol) of $N^2$-[3-[3-(1-piperidinomethyl)phenoxy]propyl]-1,3,4-thiadiazole-2,5-diamine are suspended in 150 ml of absolute tetrahydrofuran with exclusion of moisture. 3.48 ml (25 mmol) of absolute triethylamine are added and the reaction mixture is cooled to 0° C. and reacted dropwise with a solution of 1.6 (11 mmol) of 2-pyridinosulphenic acid chloride in 20 ml of absolute 1,2-dichloroethane.

After a reaction time of 1 hour at room temperature, the reaction mixture is poured into 100 ml of a saturated aqueous NaHCO₃-solution and extracted three times, each time with 100 ml of ethyl acetate. The organic phase is washed with 50 ml of a saturated aqueous NaCl solution and dehydrated over sodium sulphate, and the solvent is evaporated off under vacuum. The residue is purified by column chromatography (350 g Al₂O₃ neutral, eluant ethyl acetate/methanol 90/10).

Colorless crystals, melting point 132°–133° C.

Rf=0.2 (Al₂O₃ neutral, ethyl acetate/methanol 90/10)

Yield: 0.46 g (10% of theoretical)

C₂₂H₂₈N₆OS₂ (456.6) Calculated: C, 57.87; H, 6.18; N, 18.40; S, 14.04. Found: C, 57.71; H, 5.97; N, 18.21; S, 13.63.

¹H-NMR spectrum: (d₆-DMSO, TMS as internal standard) δ=1.18–1.63 (m) 6H, 1.95 (m) 2H, 2.15–2.42 (m) 4H, 3.17–3.70 (m) 5H (1H replaceable by D₂O), 4.00 (t) 2H, 6.67–7.97 (m) 7H, 8.47 (d) 1H, 9.37 (s, broad) replaceable by D₂O) 1H ppm.

Method B (a) Preparation of 3-[3-(hydroxymethyl)phenoxy]-propylamine

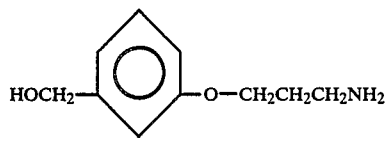

28.03 g (0.226 mol) of 3-Hydroxybenzyl alcohol are reacted with 60.47 g (0.226 mol) of bromopropylphthalimide and 5.2 g of sodium (0.226 mol) in 400 ml of ethanol at the reflux temperature (5 h). After the ethanol has been drawn off, water is added and the product is extracted with ethyl acetate. Concentration of the organic phase by evaporation yields 60.8 g of a light brown oil from which 38 g (54%) of N-[3-[3-(hydroxymethyl)phenoxy]propyl]phthalimide crystallize as a colourless solid melting at 78° to 80° C. 13.8 ml of hydrazine hydrate (80%) are added to 35.3 g (113 mmol) of N-[3-[3-(hydroxymethyl)phenoxy]propyl]phthalimide in 300 ml of ethanol and the reaction mixture is boiled under reflux for 5 hours. The ethanol is to a large extent removed by evaporation under vacuum, and 100 ml of H₂O and 40 ml of conc. HCl (pH 1) are added to the residue. The solid is removed by suction filtration and the filtrate is extracted with ethyl acetate, made alkaline with NaOH (pH 12), saturated with NaCl and extracted with 80:20 CH₂Cl₂/CH₃OH. After concentration by evaporation and distillation of the oil left behind in a bulb tube (140° to 160° C., 5/10⁻² mm Hg), 13.7 g (67% of theoretical) of a light colored solid melting at 68.5 to 69° C. are obtained.

¹H-NMR spectrum: (CDCl₃, TMS as internal standard) δ=1.86 (q) 2H, 2.37 (s, broad) 3H, 2.83 (t) 2H, 4.00 (t) 2H, 4.62 (s) 2H, 6.70–7.57 (m) 4H ppm.

(b) Preparation of 2-amino-5-[3-[3-(hydroxymethyl)phenoxy]propylamino]-1,3,4-thiadiazole

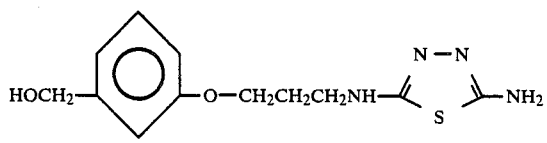

46.0 g (0.26 mol) of 5-Bromo-1,3,4-thiadiazole-2amine are stirred together with 46.3 g (0.26 mol) of 3-[3-(hydroxymethyl)phenoxy]propylamine and 71.6 ml (0.52 mol) of triethylamine in 300 ml of THF at room temperature for 30 hours. 400 ml of a saturated, aqueous solution of NaHCO₃ are added and the product is extracted with ethyl acetate. After dehydration over Na₂SO₄ and concentration by evaporation under vacuum, the residue is crystallized from ethanol/ethyl acetate.

Yield: 45.7 g (63% of theoretical)

Melting point: 94° to 95° C.

Rf=0.51 (dichloromethane/methanol 80/20)

C₁₂H₁₆N₄O₂S (280.3) Calculated: C, 51.4; H, 5.75; N, 20.0. Found: C, 51.2; H, 5.90; N, 20.0.

¹H-NMR data: (d₆-DMSO, TMF as internal standard) δ=1.97 (quin) 2H, 3.29 (q) 2H, 4.02 (t) 2H, 4.46 (d) 2H, 5.18 (t) (replaceable by D₂O) 1H, 6.24 (s) (replaceable by D₂O) 2H, 6.85–6.90 (m) 3H, 7.22 (t) 1H ppm.

(c) Preparation of 2-amino-5-[3-[3-(chloromethyl)phenoxy]propylamino]-1,3,4-thiadiazole

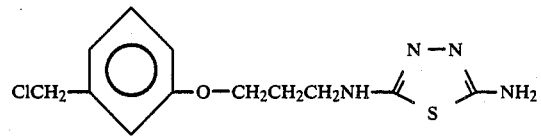

23.5 g (83 mmol) of 2-amino-5-[3-[3-(hydroxymethyl)phenoxy]propylamino]-1,3,4-thiadiazole are introduced portionwise into 120 ml of thionyl chloride under ice cooling. The reaction mixture is left to warm up to room temperature and then stirred for 2 hours and the excess thionyl chloride is evaporated off under vacuum. Water and methanol are added to the residue which is then neutralised with NaHCO₃ and extracted with 80:20 ethyl acetate/methanol. After removal of the solvent by distillation under vacuum, a beige colored solid is left behind, which is filtered over 500 g of silica gel (solvent: 90:10 CH₂Cl₂/CH₃OH). When the filtrate is concentrated by evaporation, the compound of the title is obtained as a colorless powder.

Melting Point: 135°–136° C.

Yield: 11.7 g (47% of theoretical)

Rf: 0.27 (SiO₂, 90:10 CH₂Cl₂/CH₃OH)

C₁₂H₁₅ClN₄OS (298.5) Calculated: C, 48.24; H, 5.06; N, 18.75. Found: C, 48.30; H, 5.31; N, 19.00.

¹H-NMR spectrum: (DMSO-d₆, TMS as internal standard) δ=1.98 (q) 2H, 3.33 (m) 2H, 4.04 (t) 2H, 4.72 (s) 2H, 6.23 (s) 2H (replaceable by D₂O), 6.7–7.6 (m) 5H, 1H, (replaceable by D₂O) ppm.

(d) Preparation of 5-[3-[3-(chloromethyl)phenoxy]propylamino]-2-(2-pyridinosulphenamido)-1,3,4-thiadiazole

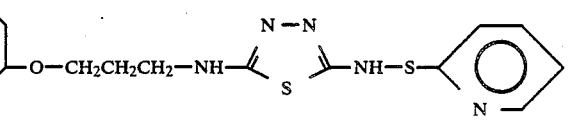

A solution of 2-pyridinosulphenic acid chloride (obtained from 1.32 g (6 mmol) of 2,2'-dithiopyridine and 0.51 ml (6.3 mmol) of SO₂Cl₂) in 15 ml of 1,2-dichloromethane is added dropwise to 2.99 g (10 mmol)

of 2-amino-5-[3-[3-(chloromethyl)phenoxy]-propylamino]-1,3,4-thiadiazole in 60 ml of absolute DMF while the temperature is maintained at 0° to 5° C. The reaction mixture is stirred for one hour under ice cooling and then left to warm up to room temperature. It is then poured out on 100 ml of a saturated NaHCO₃ solution and extracted with two 100 ml portions of ethyl acetate, and the organic phase is dehydrated over Na₂SO₄.

After concentration by evaporation under vacuum, the oily residue is chromatographed on aluminium oxide (Macherey-Nagel, neutral) (solvent: ethyl acetate followed by 90:10 ethyl acetate/methanol).

Yield: 530 mg (13% of theoretical)
Melting point: 122°–123° C.
Rf: 0.30 (Al₂O₃ neutral, 90:10 ethyl acetate/methanol)
$C_{17}H_{18}ClN_5OS_2$ (407.9) Calc.: C, 50.05; H, 4.45; N, 17.17; Cl, 8.69. Found: C, 50.15; H, 4.81; N, 17.19; Cl, 8.70.

¹H-NMR spectrum: (d₆-DMSO, TMS as internal standard) δ=1.97 (q) 1H, 3.30 (m) 2H, 4.03 (t) 2H, 4.73 (s) 2H, 6.8–7.5 (m) 7H, 1H (replaceable by D₂O), 7.85 (m) 1H, 8.50 (m) 1H, 9.37 (m) 1H (replaceable by D₂O), ppm.

(e) Preparation of 2-[3-[3-(piperidinomethyl)phenoxy]propylamino]-5-pyridine-2-sulphenamido-1,3,4-thiadiazole 816 mg (2 mmol) of 5-[3-[3-(chloromethyl)phenoxy]propylamino]-2-(2-pyridinosulphenamido)-1,3,4-thiadiazole are stirred together with 0.5 ml (5 mmol) of piperidine in 30 ml of ethanol for 3 days at room temperature. The reaction mixture is then poured out into 100 ml of a saturated, aqueous NaHCO₃ solution and extracted with ethyl acetate and dehydrated over sodium sulphate. After concentration by evaporation under vacuum, 830 mg of a yellow oil are left behind. This oil is dissolved in a small quantity of ethyl acetate, and when the solution is cooled in an ice bath, 290 mg (32% of theoretical) of the compound of the title crystallise as a colorless solid.

The physical-chemical data are identical to those obtained by Method A of Example 1b.

EXAMPLE 2

2-[3-[3-(Piperidinomethyl)phenoxy]propylamino]-5-(2-pyrimidinosulphenamido)-1,3,4-thiadiazole

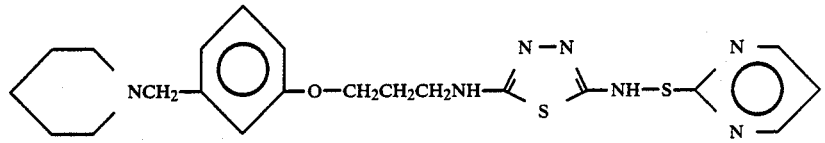

This compound is prepared by a method analogous to that of Example 1 from N²-[3-[3-(1-piperidinomethyl)phenoxy]propyl]-1,3,4-thiadiazole-2,5-diamine and 2-pyrimidinosulphenyl chloride.

Pale yellow crystals melting at 113°–116° C.
Rf=0.33 (Al₂O₃ basic/chloroform/MeOH 95/5)
$C_{21}H_{27}N_7OS_2$ (457.6)
¹H-NMR spectrum: (CDCl₃, TMS as internal standard) δ=1.20–1.70 (m) 6H, 2.05 (m) 2H, 2.20–2.47 (m) 4H, 3.43 (s, t) 4H, 4.02 (t) 2H, 6.65–7.35 (m) 7H (2H replaceable by D₂O), 8.57 (d) 2H ppm.

EXAMPLE 3

2-[3-[3-(Piperidinomethyl)phenoxy]propylamino]-5-benzene sulphenamido-1,3,4-thiadiazole

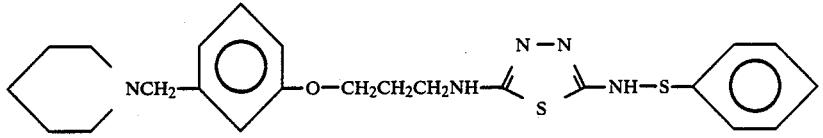

The compound is prepared by a method analogous to that of Example 1 from N²-[3-[3-(1-piperidinomethyl)phenoxy]propyl]-1,3,4-thiadiazole-2,5-diamine and benzene sulphenyl chloride.

Colorless crystals melting at 79°–80° C.
Rf=0.47 (Al₂O₃ basic/ethyl acetate/MeOH 9/1)
$C_{23}H_{29}N_5OS_2$ (455.6)
¹H-NMR spectrum: (CDCl₃, TMS as internal standard) δ=1.27–1.80 (m) 6H, 2.17 (m) 2H, 2.30–2.63 (m) 4H, 3.53 (m) 4H, 4.13 (t) 2H, 5.5–7.0 (broad) 2H (replaceable by D₂O), 6.6–7.4 (m) 9H ppm.

EXAMPLE 4

2-[3-[3-(Piperidinomethyl)phenoxy]propylamino]-5-cyclohexylsulphenamido-1,3,4-thiadiazole

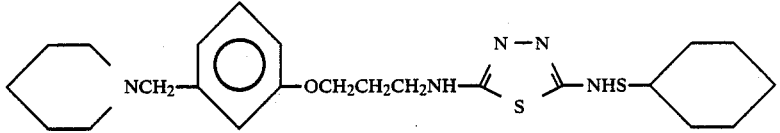

The compound is prepared by a method analogous to that of Example 1 from N²-[3-[3-(1-piperidinomethyl)phenoxy]propyl]-1,3,4-thiadiazole-2,5-diamine and cyclohexylsulphenyl chloride.

Colorless crystals melting at 129°–131° C.
Rf=0.5 (Al₂O₃ basic/ethyl acetate/MeOH 9/1)
$C_{23}H_{35}N_5OS_2$ (461.7)
¹H-NMR spectrum: (CDCl₃, TMS as internal standard) δ=1.0–2.5 (m) 22H, 2.97 (m) 1H, 3.45 (s) 2H, 3.50

(t) 2H, 4.09 (t) 2H, 6.1 (broad) 2H (replaceable by D$_2$O), 6.8–7.4 (m) 4H ppm.

EXAMPLE 5

2-[3-[3-(Piperidinomethyl)phenoxy]propylamino]-5-tolyl sulphenamido-1,3,4-thiadiazole

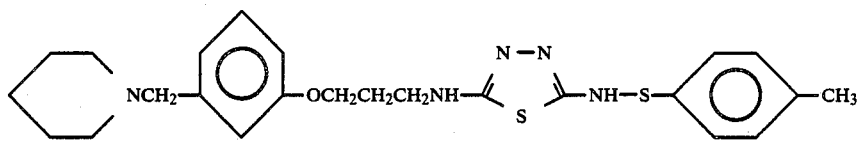

A solution of 2,37 g (15 mmol) of p-tolylsulphenyl chloride in 30 ml of 1,2-dichloroethane is added dropwise at 0° to 5° C. to 6.94 g (20 mmol) of N$^2$-[3-[3-(1-piperidinomethyl)phenoxy]propyl]-1,3,4-thiadiazole-2,5-diamine and 5.2 ml (65 mmol) of pyridine in 120 ml of absolute dimethylformamide. The reaction mixture is left to warm up to room temperature and is then poured out on 200 ml of a saturated, aqueous NHCO$_3$ solution and extracted with ethyl acetate. The organic phase is dehydrated over Na$_2$SO$_4$ and filtered. After removal of the solvent by evaporation under vacuum, the pale red, oily residue is dissolved in 150 ml of diethylether. 3.7 g of a beige coloured powder crystallizes on cooling in an ice bath, and the powder is recrystallized from 140 ml of acetone.

Yield: 2.6 g (27% of theoretical)
Colorless crystals melting at 142°–143° C.
Rf=0.38 (Al$_2$O$_3$ basic/ethyl acetate/MeOH)
C$_{24}$H$_{31}$N$_5$OS$_2$ (469.7)
$^1$H-NMR spectrum: (d$_6$-DMSO, TMS as internal standard) δ=1.40 (m) 6H 1.95 (m) 2H, 2.28 (s) (m) 7H, 3.30 (m) 2H, 3.36 (m) 3H, 1H (replaceable by D$_2$O), 3.99 (t) 2H, 6.4–7.4 (m) 8H, 9.13 (broad) 1H (replaceable by D$_2$O) ppm.

EXAMPLE 6

2-[3-[3-(Piperidinomethyl)phenoxy]-propylamino]-5-methyl sulphenamido-1,3,4-thiadiazole

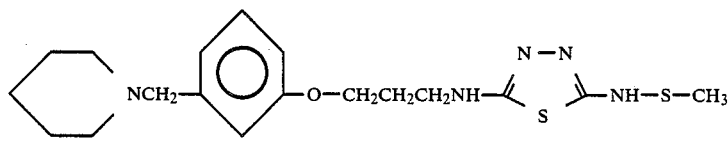

The compound is prepared by a method analogous to that of Example 5 from N$^2$-[3-[3-(1-piperidinomethyl)phenoxy]propyl]-1,3,4-thiadiazole-2,5-diamine and methylsulphenyl chloride.

Colorless crystals melting at 117°–118° C.
Rf=0.43 (Al$_2$O$_3$ basic/methyl acetate/MeOH)
C$_{18}$H$_{27}$N$_5$OS$_2$ (393.6)
$^1$H-NMR spectrum: (CDCl$_3$, TMS as internal standard) δ=1.50 (m) 6H, 2.12 (m) 2H, 2.38 (m) 4H, 2.45 (s) 3H, 3.45 (s) 2H, 3.52 (t) 2H, 4.10 (t) 2H, 5.5–6.3 (broad) 2H (replaceable by D$_2$O) 6.7–7.4 (m) 4H ppm.

EXAMPLE 7

2-[3-[3-(Piperidinomethyl)phenoxy]propylamino]-5-(2-nitrobenzenesulphenamido)-1,3,4-thiadiazole

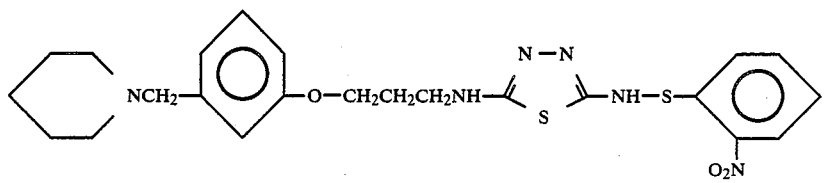

The compound is prepared by a method analogous to that of Example 5 from N$_2$-[3-[3-(piperidinomethyl)phenoxy]propyl]-1,3,4-thiadiazole-2,5-diamine and 2-nitrobenzene sulphenic acid chloride.

Yellow crystals melting at 80° to 83° C.
Rf=0.39 (Al$_2$O$_3$/methylene chloride/MeOH 95:5)
C$_{23}$H$_{28}$N$_6$O$_3$S$_2$ (500)
$^1$H-NMR spectrum: (d$_6$-DMSO, TMS as internal standard) δ=1.43 (m) 6H, 1.98 (m) 2H, 2.33 (m) 4H, 3.34 (m) 2H, 3.39 (s) 2H, 4.03 (t) 2H, 6.7–8.1 (m) 8H, 8.42 (dd) 1H, 9.53 (broad) 2H (replaceable by D$_2$O) ppm.

EXAMPLE 8

2-(Pyridine-2-sulphenamido)-5-[3-[3-(3-methylpiperidin-1-ylmethyl)phenoxy]propylamino]-1,3,4-thiadiazole

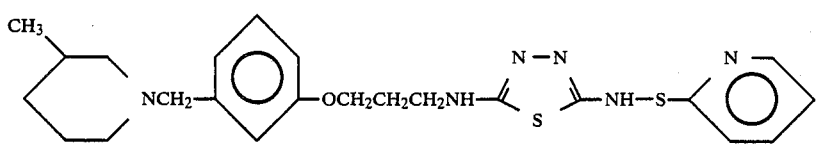

The compound is prepared by a method analogous to that of Example 5 from N$^2$-[3-[3-(3-methylpiperidin-1- ylmethyl)phenoxy]propyl]-1,3,4-thiadiazole-2,5-diamine and 2-pyridinesulphenic acid chloride.

Pale yellow crystals, melting point 118° C.
Rf=0.28 (Al$_2$O$_3$/ethyl acetate/MeOH 90:10)
C$_{23}$H$_{30}$N$_6$OS$_2$ (471)
$^1$H-NMR spectrum: (d$_6$-DMSO, TMS as internal standard) δ=0.82 (m) 4H, 1.3–2.3 (m) 8H, 2.67 (m) 2H, 3.37 (m) 2H. 3.39 (s) 2H, 4.03 (t) 2H, 6.89 (m) 3H, 7.27 (m) 4H (1H replaceable by D$_2$O), 7.87 (m) 1H, 8.53 (m) 1H, 9.3 (broad) 1H (replaceable by D$_2$O) ppm.

EXAMPLE 9

2-[3-[3-(1-Pyrrolidinomethyl)phenoxy]propylamino]-5-(2-pyridinesulphenamido)-1,3,4-thiadiazole

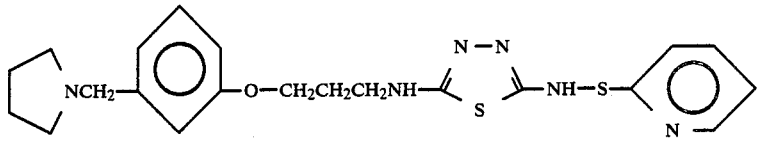

The compound is prepared by a method analogous to that of Example 5 from N$^2$-[3-[3-(1-pyrrolidinomethyl)-phenoxy]propyl]-1,3,4-thiadiazole-2,5-diamine and 2-pyridine sulphenic acid chloride.

Colorless crystals, melting point 122° C.
Rf=0.32 (Al$_2$O$_3$/ethyl acetate/MeOH 90:10)
C$_{21}$H$_{26}$N$_6$OS$_2$ (443) Calculated: C, 56.99; H, 5.92; N, 18.99. Found: C, 56.97; H, 5.99; N, 19.08.
$^1$H-NMR spectrum: (d$_6$-DMSO, TMS as internal standard) δ=1.69 (m) 4H, 1.97 (m) 2H, 2.45 (m) 4H, 3.33 (m) 2H, 3.57 (s) 2H, 4.03 (t) 2H, 6.7–7.5 (m) 7H (1H replaceable by D$_2$O), 7.7–8.0 (m) 1H, 8.50 (m) 1H, 8.7–9.8 (broad) 1H (replaceable by D$_2$O) ppm.

EXAMPLE 10

2-[3-[3-(1-Hexamethyleneiminomethyl)phenoxy]-propylamino]-5-(2-pyridinesulphenamido)-1,3,4-thiadiazole

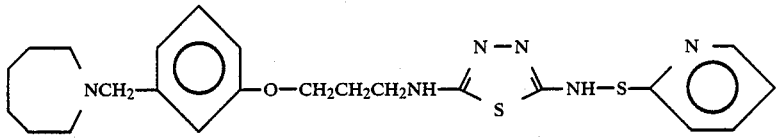

The compound is prepared by a method analogous to that of Example 5 from N$^2$-[3-[3-(1-hexamethyleneiminomethyl)phenoxy]propyl]-1,3,4-thiadiazole-2,5-diamine and 2-pyridine sulphenic acid chloride.

Colorless crystals, melting point 128° C.
Rf=0.34 (Al$_2$O$_3$/ethyl acetate/MeOH 90:10)
C$_{23}$H$_{30}$N$_6$OS$_2$ (471) Calculated: C, 58.70; H, 6.43; N, 17.86. Found: C, 58.80; H, 6.49; N, 18.08.
$^1$H-NMR spectrum: (d$_6$-DMSO, TMS as internal standard) δ=1.59 (s, broad) 8H, 1.97 (m) 2H, 2.57 (m) 4H, 3.33 (m) 2H, 3.60 (s) 2H, 4.03 (t) 2H, 6.7–7.4 (m) 7H (1H replaceable by D$_2$O), 7.7–8.0 (m) 1H, 8.5 (m) 1H, 9.3 (broad) 1H (replaceable by D$_2$O) ppm.

EXAMPLE 11

2-[4-[3-(Piperidinomethyl)phenoxy]butylamino]-5-(2-pyridinesulphenamido)-1,3,4-thiadiazole

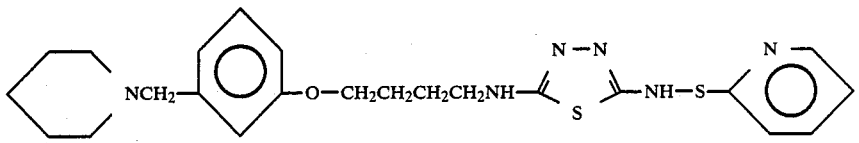

The compound is prepared by a method analogous to that of Example 5 from N$^2$-[4-[3-(piperidinomethyl)-phenoxy]butyl]-1,3,4-thiadiazole-2,5-diamine and 2-pyridine sulphenic acid chloride.

Colorless crystals melting at 121°–123° C.
Rf=0.24 (Al$_2$O$_3$/ethylacetate/MeOH 90:10)
C$_{23}$H$_{30}$N$_6$OS$_2$ (471) Calc.: C, 58.70; H, 6.43; N, 17.86. Found: C, 58.54; H, 6.50; N, 17.46.
$^1$H-NMR spectrum: (d$_6$-DMSO, TMS as internal standard) δ=1.45 (m) 6H, 1.73 (m) 4H, 2.35 (m) 4H, 3.26 (m) 2H, 3.43 (s) 2H, 4.00 (m) 2H, 6.8–7.45 (m) 7H, (1H replaceable by D$_2$O), 7.87 (m) 1H, 8.55 (m) 1H, 8.8–9.8 (broad) 1H (replaceable by D$_2$O) ppm.

EXAMPLE 12

2-[4-[3-(Piperidinomethyl)phenoxy]butylamino]-5-(4-toluenesulphenamido)-1,3,4-thiadiazole

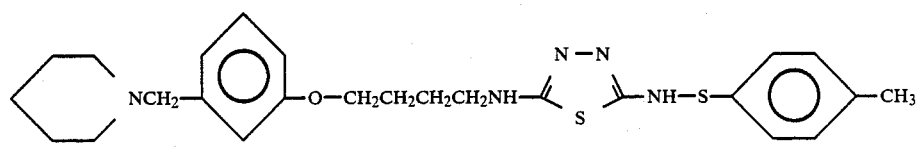

The compound is prepared by a method analogous to that of Example 5 from N$^2$-[4-[3-(piperidinomethyl)- phenoxy]butyl]-1,3,4-thiadiazole-2,5-diamine and p-tolylsulphenic acid chloride.

Colorless crystals, melting at 124°–125° C.
Rf=0.35 (Al$_2$O$_3$/ethyl acetate/MeOH 95:5)
C$_{25}$H$_{33}$N$_5$OS$_2$ (484)

$^1$H NMR spectrum: (d$_6$-DMSO, TMS as internal standard) δ=1.1–2.0 (m) 10H, 2.0–2.45 (m) 7h, 3.2 (m) 2H, 3.38 (s) 2H, 3.96 (m) 2H, 6.7–7.4 (m) 7.27 (s) 9H, (1H replaceable by D$_2$O), 9.15 (broad) 1H (replaceable by D$_2$O) ppm.

EXAMPLE 13

2-[4-[3-(Piperidinomethyl)phenoxy]butylamino]-5-cyclohexane sulphenamido-1,3,4-thiadiazole

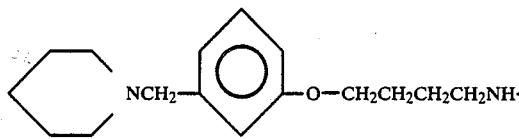

The compound is prepared by a method analogous to that of Example 5 from N$^2$-[4-[3-(piperidinomethyl)-phenoxy]butyl]-1,3,4-thiadiazole-2,5-diamine and cyclohexylsulphenic acid chloride.

Viscous oil
Rf=0.54 (Al$_2$O$_3$/ethyl acetate/MeOH 95:5)
C$_{24}$H$_{37}$N$_5$OS$_2$ (476)

$^1$H-NMR spectrum: (CDCl$_3$, TMS as internal standard) δ=1.0–2.1 (m) 20H, 2,37 (m) 4H, 2.92 (m) 1H, 3.32 (m) 2H, 3.43 (s) 2H, 3.97 (m) 2H, 5.6–6.6 (broad) 2H (replaceable by D$_2$O), 6.7–7.4 (m) 4H ppm.

EXAMPLE 14

2-[4-[3-(Piperidinomethyl)phenoxy]but-2-enylamino]-5-pyridine-2-sulphenamido-1,3,4-thiadiazole

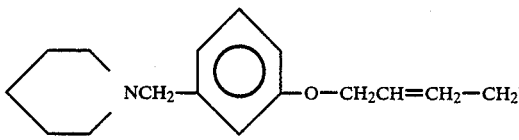

The compound is prepared by a method analogous to that of Example 5 from N$^2$-[4-[3-(piperidinomethyl)-phenoxy]but-2-enyl]-1,3,4-thiadiazole-2,5-diamine and 2-pyridine sulphenic acid chloride.

Colorless crystals, melting at 129°–130° C.
Rf=0.54 (Al$_2$O$_3$/ethyl acetate/MeOH 80:20)
C$_{23}$H$_{28}$N$_6$OS$_2$ (469) Calculated: C, 58.95; H, 6.02; N, 17.93. Found: C, 58.90; H, 6.03; N, 17.94.

$^1$H-NMR spectrum: (d$_6$-DMSO, TMS as internal standard) δ=1.42 (m) 6H, 2.32 (m) 4H, 3.40 (s) 2H, 3.87 (m) 2H, 4.53 (m) 2H, 5.93 (m) 2H, 6.89 (m) 3H, 7.1–7.5 (m) 4H (1H replaceable by D$_2$O), 7.7–8.0 (m) 1H, 8.50 (m) 1H, 9.0–9.7 (broad) 1H (replaceable by D$_2$O) ppm.

We claim:

1. 1,3,4-Thiadiazole derivatives corresponding to the general formula I

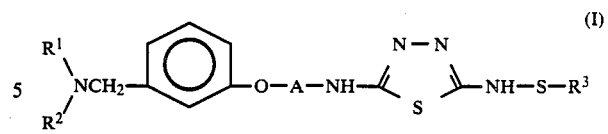

wherein R$^1$ and R$^2$, which may be identical or different, each represents hydrogen, straight chained C$_1$-C$_{10}$-alkyl, C$_5$-C$_6$-cycloalkyl, C$_1$-C$_3$-alkylamino or di-(C$_1$-C$_3$-alkyl)-amino or R$^1$ or R$^2$ together with the nitrogen atom to which they are attached form a ring selected from the group consisting of pyrrolidine, piperidine and homopiperidine, optionally mono- or di-substituted with a C$_1$-C$_3$-alkyl group; A represents the group —(CH$_2$)$_n$— or —CH$_2$—CH=CH—CH$_2$, wherein n has the value 3 or 4; R$^3$ represents straight chained or branched C$_1$-C$_6$-alkyl or C$_5$-C$_6$-cycloalkyl or unsubstituted or mono- to tri-substituted phenyl or naphthyl or hetero aryl selected from the group consisting of 2-pyridyl and 2-pyrimidinyl wherein substitutents in the substituted phenyl or naphthyl or hetero aryl are selected from the group consisting of halogen, straight chained or branched alkyl having from 1 to 6 carbon atoms, alkoxy having from 1 to 6 carbon atoms or trifluoromethyl, or nitro and the physiologically acceptable salts thereof.

2. Compounds according to claim 1, wherein R$^3$ represents straight chained or branched C$_1$-C$_6$-alkyl or C$_5$-C$_6$-cycloalkyl.

3. Compounds according to claim 1, wherein R$^3$ represents unsubstituted or mono- or tri-substituted aryl.

4. Compounds according to claim 1, wherein R$^3$ represents a pyridine or pyrimidine ring.

5. Compounds according to any one of claims 1 to 4, wherein R$^1$ and R$^2$ together with the nitrogen atom to which they are attached form a pyrrolidine, piperidine or homopiperidine ring and that A represents the group —(CH$_2$)$_3$— or —CH$_2$—CH=CH—CH$_2$—.

6. 2-[3-[3-(Piperidinomethyl)phenoxy]propylamino]-5-pyridine-2-sulphenamido-1,3,4-thiadiazole and the physiologically acceptable salts thereof.

7. 2-[4-[3-(Piperidinomethyl)phenoxy]butylamino]-5-cyclohexanesulphenamido-1,3,4-thiadiazole and the physiologically acceptable salts thereof.

8. 2-(Pyridine-2-sulphenamido)-5-[3-[3-(3-methyl-piperidin-1-yl-methyl)-phenoxy]propylamino]-1,3,4-thiadiazole and the physiologically acceptable salts thereof.

9. 2-[4-[3-(Piperidinomethyl)phenoxy]butylamino]-5-(2-pyridinesulphenamido)-1,3,4-thiadiazole and the physiologically acceptable salts thereof.

10. Pharmaceutical compositions containing a histamine-H$_2$ receptor inhibitory amount of compound according to claims 1 to 6 and at least one inert, pharmaceutically acceptable carrier or an inert, pharmaceutically acceptable diluent.

* * * * *

UNITED STATES PATENT AND TRADEMARK OFFICE
CERTIFICATE OF CORRECTION

PATENT NO. : 4,738,960

DATED : April 19, 1988

INVENTOR(S) : Helmut Schickaneder et al

It is certified that error appears in the above-identified patent and that said Letters Patent is hereby corrected as shown below:

Claim 3 (column 16, line 43), after "mono-", "or" should be --to--.

Signed and Sealed this

Nineteenth Day of July, 1988

*Attest:*

DONALD J. QUIGG

*Attesting Officer*     *Commissioner of Patents and Trademarks*